United States Patent
Gutierrez (12)

(10) Patent No.: US 6,372,242 B1
(45) Date of Patent: Apr. 16, 2002

(54) COLLAR CONTAINING A NOVEL GEL FORMULATION TO CONTROL ARTHROPOD INFESTATION OF ANIMALS

(75) Inventor: Luis Gutierrez, Lincoln, NE (US)

(73) Assignee: Pfizer Inc, New York, NY (US)

(*) Notice: Subject to any disclaimer, the term of this patent is extended or adjusted under 35 U.S.C. 154(b) by 0 days.

(21) Appl. No.: 09/366,524

(22) Filed: Aug. 3, 1999

Related U.S. Application Data

(60) Provisional application No. 60/095,684, filed on Aug. 7, 1998.

(51) Int. Cl.[7] ............................................. A01N 25/10
(52) U.S. Cl. ...................... 424/411; 424/403; 424/406; 514/68; 514/136; 514/318; 514/345; 514/579; 514/531; 637/784; 637/785; 637/876; 637/919
(58) Field of Search ............................ 514/531, 68, 88, 514/98, 59, 579, 758, 318, 345, 637, 136, 784, 785, 919, 876; 424/403, 405, 406, 411

(56) References Cited

U.S. PATENT DOCUMENTS

| | | | |
|---|---|---|---|
| 2,791,202 A | 5/1957 | Doyle | 119/106 |
| 4,544,547 A | 10/1985 | von Bittera et al. | 424/14 |
| 4,792,450 A | 12/1988 | Kydonieus et al. | 424/449 |
| 4,879,117 A | 11/1989 | Rombi | 424/411 |
| 5,266,324 A | 11/1993 | Stendel et al. | 424/411 |
| 5,294,445 A | 3/1994 | Sieveking et al. | 424/411 |
| 5,296,227 A | 3/1994 | Norval et al. | 424/411 |
| 5,437,869 A | 8/1995 | Kelley | 424/406 |
| 5,632,999 A | 5/1997 | Miller | 424/411 |
| 5,641,480 A | * 6/1997 | Vermeer | 424/70.24 |
| 5,660,844 A | 8/1997 | Christie et al. | 424/411 |
| 5,948,423 A | * 9/1999 | Karg | 424/409 |
| 6,184,277 B1 | 2/2001 | Bara | 524/268 |

FOREIGN PATENT DOCUMENTS

| | | | |
|---|---|---|---|
| DK | 2754249 | * | 6/1978 |
| GB | 2099303 | | 12/1982 |
| GB | 2111830 | * | 7/1983 |
| JP | 6256048 | | 9/1988 |
| JP | 7046955 | | 2/1995 |
| WO | 9201375 | | 2/1992 |
| WO | 9731623 | | 9/1997 |
| ZA | 8107644 | | 10/1982 |

* cited by examiner

*Primary Examiner*—Neil S. Levy
(74) *Attorney, Agent, or Firm*—Peter C. Richardson; Paul H. Ginsburg; Alan L. Koller

(57) ABSTRACT

The present invention provides a device, preferably a collar or ear tag, capable of the controlled, sustained release of an effective amount of an active ingredient that can protect an animal against arthropod pests, comprising a reservoir containing a novel gel formulation comprising a fatty acid, an organic solvent which is a linear aliphatic ester, a silicone-based fluid, or a combination thereof, and an active ingredient that can protect the animal against one or more arthropod pests.

29 Claims, 1 Drawing Sheet

Figure 1:
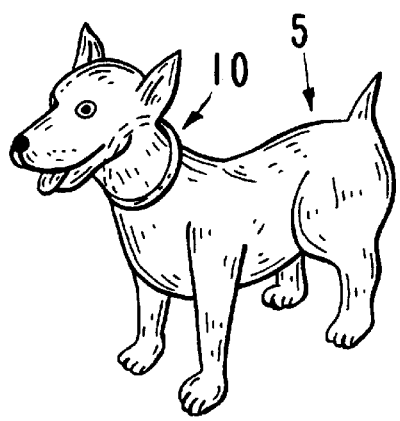

COLLAR CONTAINING A NOVEL GEL FORMULATION TO CONTROL ARTHROPOD INFESTATION OF ANIMALS

This application claims priority to the Provisional Application No. 60/095,684 filed Aug. 7, 1998.

1. FIELD OF THE INVENTION

This invention relates generally to the field of devices useful in protecting animals against arthropod pests. The invention relates more specifically to collar and ear tag devices capable of the controlled, sustained release of an effective amount of an active ingredient that can protect an animal against arthropod pests, wherein the active ingredient is part of an improved gel formulation contained within such devices.

2. BACKGROUND OF THE INVENTION

Various methods have been employed to protect animals against arthropod pests, particularly fleas, ticks, flies, and mites. Customarily, animals have been sprayed with or dipped in an insecticide solution. However, this type of treatment provides only temporary protection, usually lasting less than three weeks as the result of degradation by various environmental factors such as sunlight, moisture, etc.

Attempts to improve and simplify the control of arthropod pests have previously involved providing a device, such as a collar or ear tag comprising an insecticide, to be worr by the animal. For domesticated pets such as dogs and cats, insecticidal collars have beer used which comprise a solid matrix material impregnated with an insecticidal composition that is released from the collar and spread when the collar rubs against the animal's coat. Ear tags, which have been used in an attempt to control arthropod pests of livestock, also comprise a solid matrix material impregnated with an insecticidal composition that is released and spread when the tag rubs against the animal's coat. However, the protection offered by such collar and ear tag devices is unreliable and short-lived, partially because the solid matrix material is inefficient at releasing the insecticidal composition.

U.S. Pat. No. 5,660,844 to Christie et al. refers to collar and ear tag devices to protect animals against arthropod infestation, which devices comprise a gel enclosed in a cavity inside a reservoir. The gel referred to includes a combination of a wax gelling agent, an organic solvent such as mineral oil, and an insecticidal composition. These devices are generally more effective and provide longer lasting protection than prior devices and methods However, as much as three to five weeks are required for an effective amount of the active ingredient to permeate through the wall of the reservoir after manufacture. In addition, a gel that comprises mineral oil can leave an oily deposit on the animal's coat. Furthermore, mineral oil is known to irritate the skin of some animals. Still further, contamination of the open ends of the tube of the reservoir with such a gel often inhibits the tube from being adequately sealed during manufacture. Still further, certain insecticides such as cypermethrin are not miscible in such a gel.

A need therefore exists for collar and ear tag devices comprising an improved gel formulation that requires a shorter time period for an effective amount of the active ingredient to permeate through the wall of the reservoir after manufacture, that does not leave an oily residue on the animal's coat or irritate the skin, that does not inhibit the sealing of the reservoir, and in which insecticides such as cypermethrin are miscible.

3. SUMMARY OF THE INVENTION

In one aspect, the present invention provides a device capable of the controlled, sustained release of an effective amount of an active ingredient that can protect an animal against arthropod pests such as fleas, ticks, flies, and mites. The device comprises a reservoir having a supporting membrane comprising an outside surface, and an inside surface defining an enclosed cavity, and a gel contained within the enclosed cavity and in contact with the inside surface, said gel comprising the admixture of a gelling agent which is a fatty acid or salt thereof, an organic solvent which is a linear aliphatic ester, a silicone-based fluid, or a combination thereof, and an active ingredient dispersed therein that can protect the animal against one or more arthropod pests, wherein the supporting membrane of the reservoir comprises a polymeric material that is permeable to the active ingredient. In a preferred though non-limiting embodiment, the supporting membrane of the reservoir is polyvinyl chloride (PVC), the fatty acid is stearic acid, the organic solvent is a combination of methyl palmitate and a silicone-based fluid such as dimethicone, and the active ingredient is an insecticide, an insect repellant, or an insect growth regulator (IGR), or a combination thereof. In a further preferred embodiment, the weight ratio of methyl palmitate and dimethicone in the organic solvent is about 50 weight % (wt %) methyl palmitate and about 50 wt % dimethicone In a particularly useful embodiment, the gel comprises from about 45 wt % to about 55 wt % stearic acid, from about 15 wt % to about 25 wt % organic solvent, and from about 18 wt % to about 28 wt % active ingredient. The gel can further comprise one or more additional components, including stabilizers such as anti-oxidants or ultraviolet light blockers, as needed. The device of the present invention is preferably in the form of a collar or ear tag which further comprises a fastening means for fastening the device around the neck or to the ear, respectively, of the animal.

In still another aspect, the present invention provides a gel in an improved formulation for use in a collar or ear tag device to protect an animal against arthropod pests, which gel comprises the admixture of a gelling agent which is a fatty acid or salt thereof, an organic solvent which is a linear aliphatic ester, a silicone-based fluid, or a combination thereof, and an active ingredient dispersed therein that can protect the animal against one or more arthropod pests.

In still another aspect, the present invention provides a method of preparing a device capable of the controlled, sustained release of an effective amount of an active ingredient that can protect an animal against arthropod pests, which device comprises a reservoir having a supporting membrane comprising an outside surface, and an inside surface defining an enclosed cavity, and a gel contained within the enclosed cavity and in contact with the inside surface, said gel comprising the admixture of a gelling agent which is a fatty acid or salt thereof, an organic solvent which is a linear aliphatic ester, a silicone-based fluid, or a combination thereof, and an active ingredient dispersed therein that can protect the animal against one or more arthropod pests, wherein the supporting membrane of the reservoir comprises a polymeric material that is permeable to the active ingredient, which method comprises filling a cavity defined by the inside surface of the supporting membrane with the gel and sealing the supporting membrane so as to enclose the gel in the cavity.

In still another aspect, the present invention provides a method of protecting animals against arthropod pests, comprising the step of fastening the device of the present invention, e.g., as a collar or ear tag, to the animal.

4. BRIEF DESCRIPTION OF THE DRAWINGS

FIG. 1. Example of a device of the present invention wherein the reservoir is configured as a tube collar and is worn by a dog.

Figure 2:
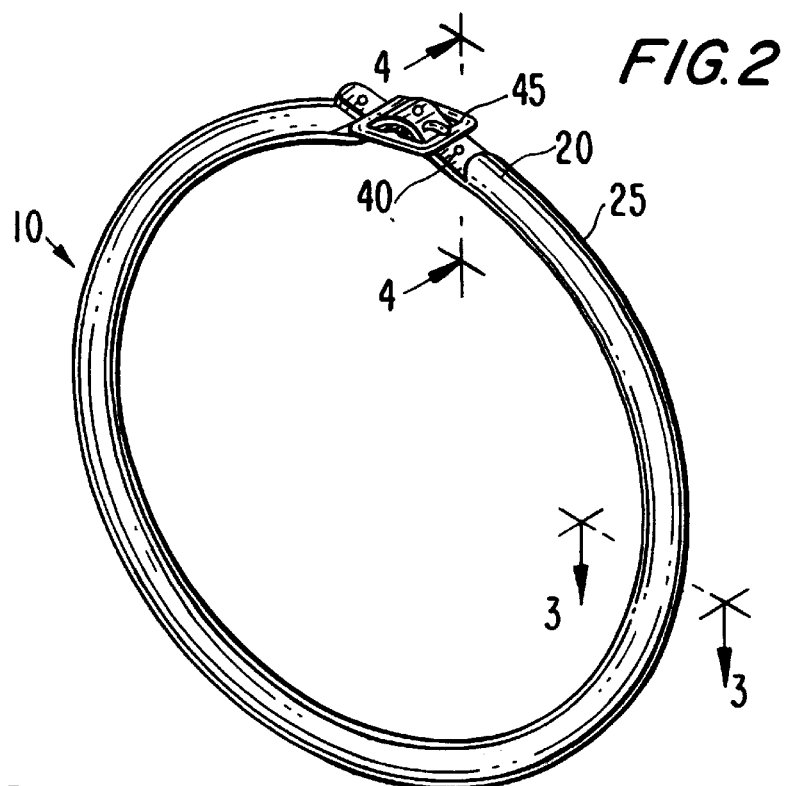

FIG. 2. Perspective view of a reservoir configured as a tube collar and further comprising a buckle fastening means.

Figure 3:
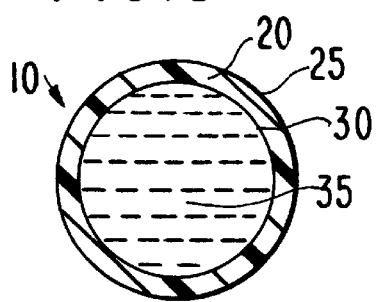

FIG. 3. Cross-sectional view through the tube collar device of FIG. 2.

Figure 4:
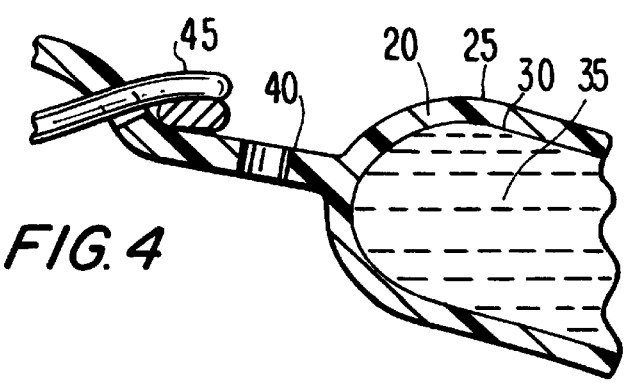

FIG. 4. Side-sectional view through the tube collar device of FIG. 2.

5. DETAILED DESCRIPTION OF THE INVENTION

The present invention provides a device capable of the controlled, sustained release of an effective amount of an active ingredient that can protect an animal against arthropod pests such as fleas, ticks, flies, and mites. The device of the present invention comprises a reservoir having a supporting membrane comprising an outside surface, and an inside surface defining an enclosed cavity, and a gel contained within the enclosed cavity and in contact with the inside surface of the supporting membrane, which gel comprises the active ingredient dispersed therein.

The material comprising the supporting membrane of the reservoir is preferably selected to have the desired physical properties of permeability and chemical inertness. Thus, the material comprising the supporting membrane of the reservoir must be permeable to the active ingredient in the gel. Furthermore, the material comprising the supporting membrane of the reservoir preferably should not substantially react with any of the components of the gel. The supporting membrane of the reservoir is preferably a polymeric material which is selected from the group consisting of porous tetrafluoroethylene, polyethylene, polypropylene, polyamide, flexible polyacrylate, polyvinyl chloride (PVC), ethylenevinylacetate, polyolefin, polyurethane, silicone, and combinations thereof. Flexible polymeric material is preferred because it can be more easily adapted to fit an animal and is more amenable to controlling the release rate of the active ingredient by adjusting the wall thickness. In a preferred though non-limiting embodiment, the flexible polymeric material is PVC tubing, e.g., Tygon® R-3603 tubing, which is commercially available, among other places, from Norton Performance Plastics (Akron, Ohio).

The reservoir of the device of the present invention can be any desired shape so long as it can be fastened to an animal and serve to protect that animal against arthropod pests. As used herein, the device of the present invention "protects" an animal against arthropod pests where the device, when fastened to the animal, prevents or eliminates infestation of the animal by one or more arthropod pests, such as fleas, ticks, flies or mites, or significantly reduces the number of any one or more of such arthropod pests infesting, alighting on, or swarming around the animal at a time at which the device is effective, as compared to an untreated control group.

In a preferred though non-limiting embodiment, the reservoir is tube-shaped, where the inside surface of the supporting membrane comprising the reservoir is the inside diameter of the tube, and the outside surface of the supporting membrane comprising the reservoir is the outside diameter of the tube. In a preferred though non-limiting embodiment, a tube-shaped reservoir can be wrapped as a collar around the neck of an animal. Collars of any suitable length can be easily fabricated depending upon the neck size of the animal. Typically, the collar is selected to be about 6 to about 24 inches in length. In such a collar, the cavity enclosed within the reservoir is between about 5 and about 15 inches in length, respectively, the supporting membrane of the reservoir is between about $\frac{1}{32}$ to about $\frac{1}{8}$ of an inch thick (i.e., the distance between the inside and the outside surfaces), and the reservoir extends in about 1 to about 5 inch tabs beyond each end of the enclosed cavity depending upon the neck size of the animal. The ends of the collar can further comprise fastening means. For example, a first end of the collar can comprise a first part, and the second end of the collar can comprise a second part, of a two-part type fastening means, such as a buckle, snap, or hook and loop type fastener such as a Velcro® fastener. Where the reservoir is configured as an ear tag, the device further comprises an appropriate ear tag fastening means as known in the art such as, e.g., a clip.

Reference is made to the appended drawings to demonstrate a non-limiting embodiment of the present invention. FIG. 1 is an example of a device of the present invention wherein the reservoir 10 is configured as a tube collar and is worn by a dog 5. FIG. 2 is a perspective view of the reservoir 10 configured as a tube collar, further exemplifying the use of a buckle fastening means 45. FIG. 3 is a cross-sectional view through the tube collar of FIG. 2, showing the reservoir 10 comprising a supporting membrane 20, the outside surface 25 of the supporting membrane 20, the inside surface 30 of the supporting membrane 20 which defines an enclosed cavity, and a gel 35 contained within the enclosed cavity and in contact with the inside surface 30 of the supporting membrane 20. FIG. 4 is a side-sectional view through the tube collar of FIG. 2, showing the reservoir 10 comprising a supporting membrane 20, the outside surface 25 of the supporting membrane 20, the inside surface 30 of the supporting membrane 20 which defines an enclosed cavity, a gel 35 contained within the enclosed cavity and in contact with the inside surface 30 of the supporting membrane 20, a tab 40 extending beyond the end of the enclosed cavity, and a portion of the buckle fastening means 45.

The gel of the device of the present invention is an improved formulation which comprises a gel composition and one or more active ingredients dispersed therein. As used herein, the term "gel composition" refers to a semi-solid, organic gel composition, i.e., a gel composition which contains an organic solvent, as opposed to a hydrogel which contains water. The components comprising the gel composition are a gelling agent and an organic solvent which are generally chosen so as to be compatible for use with lipophilic compounds.

The gelling agent is selected to create the gel composition upon combination with an appropriate organic solvent. The gelling agent is preferably a fatty acid having an unbranched hydrocarbon chain from about $C_{15}$ to about $C_{17}$ in length. In a more preferred embodiment, the gelling agent is a saturated fatty acid such as palmitic acid or stearic acid, or a combination thereof. In a more preferred embodiment, the gelling agent is stearic acid, which is generally available from commercial sources, such as Fisher Scientific, Inc. The gelling agent can alternatively be a salt, such as the calcium salt, of a fatty acid. For example, the gelling agent can be calcium distearate.

Suitable organic solvents can be selected from: (a) linear aliphatic ester solvents characterized by having from about 9 carbons to about 17 carbons in the chain; (b) silicone fluids, which are blends of high molecular weight silicone polymers dispersed in a low viscosity silicone oil; and (c) combinations of such linear aliphatic ester solvents and silicone fluids. In a preferred though non-limiting embodiment, the linear aliphatic ester solvent is selected from the group consisting of methyl caproate, methyl caprylate, methyl myristate and methyl palmitate. Silicone fluids that are useful in practicing the present invention can have a range of viscosities, e.g., from about 5 to about 50 centistokes (cst). In a preferred though non-limiting embodiment, the silicone fluid is selected from the group consisting of cyclomethicone, dimethicone, dimethicone copolyol, trimethylsilylamodimethicone, and a combination thereof. In a particularly preferred embodiment, the organic solvent of the gel composition is a combination of methyl palmitate, which is commercially available from Aldrich Chemical Co., and dimethicone (SF-96 (5 cst)), which is commercially available from General Electric Co. In all specific embodiments described below, the term "dimethicone" refers to dimethicone (SF-96 (5 cst)), although the invention of the present invention is not limited to the use of this specific dimethicone formulation.

When the organic solvent of the gel composition consists of a mixture of methyl palmitate and dimethicone, these two components are preferably present in a weight range of from about 10 wt % to about 90 wt % methyl palmitate and, accordingly, from about 90 wt % to about 10 wt % dimethicone, and more preferably from about 40 wt % to about 60 wt % methyl palmitate and, accordingly, from about 60 wt % to about 40 wt % dimethicone. In a particularly preferred embodiment, the organic solvent consists of about 50 wt % methyl palmitate and about 50 wt % dimethicone, which mixture is particularly desirable when utilizing PVC as the supporting membrane of the reservoir.

In a preferred embodiment, the gelling agent is present in the gel in a range of from about 45 wt % to about 55 wt %, more preferably from about 48 wt % to about 54 wt %, and most preferably from about 50 wt % to about 52 wt %. In a preferred embodiment, the organic solvent is present in the gel in the range of from about 15 wt % to about 25 wt %, and more preferably from about 16 wt % to about 22 wt %.

The gel further comprises one or more active ingredients, which are preferably selected from insecticides, insect repellants, and insect growth regulators (IGR). In a preferred embodiment, the active ingredient is an insecticide that can protect an animal against arthropod pests, such as those that commonly infest, alight on, or swarm around dogs, cats, cattle, horses, sheep or goats. Such arthropod pests typically include fleas, ticks, flies, and mites, as well as lice and other ectoparasites.

A wide variety of such active ingredients are known and may be readily selected based on the particular arthropod pest to be controlled and the animal to be treated. Suitable insecticides include chlorinated hydrocarbons, organophosphates, pyrethrins, pyrethroids, and carbamates. Non-limiting examples of such insecticides are those identified by the common names lindane, methoxychlor, permethrin, cypermethrin, dichlorvos, diazinon, chlorfenvinphos, bendiocarb, amitraz, chlorpyrifos, deltamethrin and sevin. In a preferred embodiment, the active ingredient is a pyrethroid, which class of insecticides is particularly well-suited for the treatment of fleas and ticks. Suitable insect repellants include DEET, citronella, permethrin, pyrethrin, among others. Suitable IGRs include methoprene, hydroprene, S-methoprene, S-hydroprene, dimilin (diflupenzeron), and chromazine, among others. These and other insecticides, insect repellants, and IGRs, as known in the art, can be used alone or in combination as active ingredients in the gel of the present invention.

Alternatively or additionally, the gel may contain an endectocide such as doramectin, ivermectin, avermectin, or moxidectin, among others, which are commercially available. Alternatively or additionally, the gel can include one or more other active ingredients such as a medication for treating a disease or condition in the animal, which medication can be effectively delivered by topical application to the animal using the device of the present invention and which medication is compatible with the improved gel formulation of the present invention. Examples of such medicines include those, such as allantoin, which are useful in treating skin irritations. Ultimately, the active ingredient is chosen so as to be miscible in the organic solvent of the gel composition. The gel can additionally include other ingredients that serve to enhance the delivery, absorption, or effectiveness of the active ingredient, such as surfactants or other detergents.

The amount of active ingredient to be included in the gel depends upon several factors, including the size of the animal, the particular active ingredient utilized, and the nature and extent of the particular pest problem. The active ingredient is preferably included in the gel in an amount that is in excess of the amount required to effectively protect the particular animal against arthropod pests so as to ensure that at least the appropriate effective amount of the active ingredient reaches the animal over a prolonged period of time. To be effective, the amount of active ingredient in the gel should generally be sufficient to provide about 6 mg/day to about 24 mg/day of active ingredient to the animal. For example, for a dog weighing about 7 kg, a delivery of about 6 mg/day to about 16 mg/day is preferred. For a dog weighing about 16 kg, a delivery of about 10 mg/day to about 24 mg/day is preferred. In a preferred embodiment, the active ingredient should comprise from about 18 wt % to about 28 wt % of the gel, more preferably from about 20 wt % to about 26 wt %, and most preferably from about 22 wt % to about 24 wt %, although these weight percentages can vary significantly depending upon the factors listed above.

With a sufficient amount of active ingredient in the gel, the device of the present invention can deliver an effective amount of the active ingredient onto the surface of an animal over an extended period of time, and generally for at least 180 days. An "effective amount" of active ingredient refers to an amount of active ingredient that is capable of preventing or eliminating infestation of the animal by one or more arthropod pests, such as fleas, ticks, flies or mites, or significantly reducing the number of any one or more of such arthropod pests that are infesting, alighting on, or swarming around the animal, as compared to an untreated control group.

The gel of the present invention can further comprise additional components as needed. For example, antioxidants such as butoxyhydroxytoluene (BHT), sodium sulfite, pyrazolone, or thioglycolic acid can be added to the gel at from about 1 wt % to about 7 wt % to inhibit or avoid oxidation of the active ingredient. Alternatively or additionally, ultraviolet light blockers, such as octyl dimethyl PABA, octyl methoxycinnamate, benzophenone 3, octyl salicylate or octocrylene can be added to the gel at from about 1 wt % to about 7 wt % to protect against damage to the active ingredient from sunlight. These anti-oxidants and ultraviolet light blockers serve as stabilizers to prolong the life of the active ingredient. For example, for devices that are to be used predominantly outside, e.g., on livestock, from about 1 wt % to about 7 wt % of octyl methoxycinnamate can be added to the gel to protect against damage from sunlight. The gel can further comprise a deodorant, perfume or colored dye, or a combination thereof, as needed.

In a particularly effective though non-limiting embodiment, a gel formulation for use in a device of the present invention can comprise from about 45 wt % to about 55 wt % stearic acid, from about 15 wt % to about 25 wt % organic solvent (which is typically about 50 wt % methyl palmitate and about 50 wt % dimethicone), and from about 18 wt % to about 28 wt % cypermethrin as active ingredient. Optional components such as anti-oxidants and UV blockers are present in a weight range of from about 1 wt % to about 7 wt % each.

In a non-limiting embodiment, using a gel comprising cypermethrin by way of example, an effective collar device can made to the following parameters. PVC tubing is selected having a membrane thickness of between about 1/32 and about 1/16 of an inch; the preferred fill length of the tube is about 5 to about 11 inches; and the gel comprises about 51 wt % stearic acid, about 10 wt % methyl palmitate, about 10 wt % dimethicone, about 22 wt % cypermethrin, and about 7 wt % total optional ingredients including an anti-oxidant and an ultraviolet light blocker.

The release rate of the active ingredient from the reservoir is related to, among other factors, the porosity, permeability and thickness of the supporting membrane, the concentration and molecular weight of the active ingredient, and the weight ratio of the various components comprising the particular gel. The release rate of the active ingredient can be controlled by systematically altering one or more of these parameters. It is possible to regulate the release rate of an active ingredient from the reservoir by adjusting the amount of organic solvent in the gel, or by selecting a supporting membrane material having a different porosity or permeability, or by carrying out a combination of such modifications. For example, as the molecular weight of the active ingredient increases, its release rate from a particular reservoir will generally decrease. Thus, e.g., if the active ingredient is a molecule having a larger molecular weight than cypermethrin and the same release rate is required as for cypermethrin, then a gel comprising a larger percentage of organic solvent can be prepared, or a more porous or thinner supporting membrane material can be selected. Alternatively, if the active ingredient is a molecule having a smaller molecular weight than cypermethrin and the same release rate is required as for cypermethrin, then a gel comprising a smaller percentage of organic solvent can be prepared, or a less porous or thicker supporting membrane material can be selected. By adjustment of these and other parameters, the release rate of the active ingredient can be optimized for any particular device or circumstance.

In a non-limiting embodiment, the release rate of the active ingredient from a reservoir, assuming a constant supporting membrane thickness, can be varied by adjusting the solvent content of the gel to produce a "softer" or "harder" gel. Using a gel comprising cypermethrin by way of example, a relatively softer gel can comprise about 48 wt % stearic acid, about 11.8 wt % methyl palmitate, about 11.9 wt % dimethicone, about 20 wt % cypermethrin, about 4.5 wt % ultraviolet light blocker, and about 3.8 wt % anti-oxidant. A relatively harder gel can comprise about 53.4 wt % stearic acid, about 9.1 wt % methyl palmitate, about 9.2 wt % dimethicone, about 20 wt % cypermethrin, about 4.5 wt % ultraviolet light blocker, and about 3.8 wt % anti-oxidant.

To prepare the device of the present invention, a gel is prepared by combining together the organic solvent, the gelling agent, the active ingredient, and any other additives. The combined ingredients are typically heated to about 80° C. with mixing until a homogenous liquid mixture is achieved. The homogenization process typically takes about 4 hrs at atmospheric pressure. When the gelling agent is stearic acid, and the organic solvent is 50 wt % dimethicone and 50 wt % methyl palmitate, the mixture can be prepared by heating to a temperature of between about 80° and about 90° C. After homogenization, and upon cooling, this particular mixture will begin to gel at about 65° C. Appropriate temperatures of preparation for other gels useful in practicing the present invention can be readily determined by the skilled artisan.

The cavity of the reservoir is filled with the homogenized liquid mixture. After filling, the cavity is sealed shut by heat or by any other method effective to accomplish a complete sealing of the supporting membrane material so as to enclose the gel. A particularly suitable method of sealing PVC tubing is by using radio frequency sealing equipment, such as that which is commercially available from Fabricacione Electronicas (Buenos Aires, Argentina). Once the reservoir is filled with the gel and sealed, an effective amount of the active ingredient typically permeates through the supporting membrane in about 3 days, and the device is then ready for use.

The device of the present invention provides for the controlled, sustained release of an effective amount of an active ingredient that can protect an animal against arthropod pests such as fleas, ticks, flies, and mites. The release is "controlled" because its rate can be adjusted by altering one or more parameters described above. The release is also "sustained" because it occurs continuously over an extended period of time, e.g., for at least 180 days after manufacture, without interruption. The active ingredient of the gel in the enclosed cavity continuously permeates through the wall of the reservoir and is distributed onto the animal's coat by a combination of the chemical nature of the supporting membrane and the components comprising the gel, the movement of the device against the animal's coat, and the interaction of the active ingredient and organic solvent with the body oil of the animal.

The improved formulation of the gel of the present invention provides superior results compared to prior formulations by requiring a shorter time period for an effective amount of the active ingredient to permeate through the supporting membrane of the reservoir. Thus, the improved gel formulation allows permeation of an effective amount of the active ingredient to occur in about 3 days, as compared to about 3 to 5 weeks for prior formulations. As a result of this shortened initial permeation period, the device is ready for use more quickly after manufacture, thereby reducing or eliminating the amount of time that such devices must be stored prior to use. Additional advantages of the device of the present invention include eliminating several of the problems associated with the use of a mineral oil-based gel, such as leaving an oily residue on the animal, the potential for triggering skin irritations, and inhibiting the process of sealing the reservoir. In addition, insecticides such as cypermethrin which are not miscible in mineral oil-based gels are miscible in the improved gel formulation of the present invention. An added benefit has been observed relating to the ability of the improved gel formulation of the present invention to produce a noticeably fluffier coat on the animal, which may be attributable to the emollient characteristics of the silicone fluid component of the organic solvent.

The present invention further provides a gel for use in a collar or ear tag device which is capable of the controlled, sustained release of an effective amount of an active ingredient that can protect an animal against arthropod pests, which gel comprises the admixture of a gelling agent which is a fatty acid or salt thereof, an organic solvent which is a linear aliphatic ester, a silicone-based fluid, or a combination thereof, and an active ingredient dispersed therein that can protect the animal against one or more arthropod pests, as described above.

The present invention further provides a method of preparing a device capable of the controlled, sustained release of an effective amount of an active ingredient that can protect an animal against arthropod pests, which device comprises a reservoir having a supporting membrane comprising an outside surface, and an inside surface defining an enclosed cavity, and a gel contained within the enclosed cavity and in contact with the inside surface, said gel comprising the admixture of a gelling agent which is a fatty acid or salt thereof, an organic solvent which is a linear aliphatic ester, a silicone-based fluid, or a combination thereof, and an active ingredient dispersed therein that can protect the animal against one or more arthropod pests, wherein the supporting membrane of the reservoir comprises a polymeric material that is permeable to the active ingredient, which method comprises filling a cavity defined by the inside surface of the supporting membrane with the gel and sealing the supporting membrane so as to enclose the gel in the cavity.

The present invention further provides a method of protecting an animal against arthropod pests, comprising the step of fastening the device of the present invention to the animal. A collar device of the present invention can be fastened around the animal's neck by using a suitable collar fastening means, as known in the art. An ear tag device of the present invention can be fastened to the animal's ear by using a suitable ear fastening means, as known in the art, e.g., by use of a clip. Alternatively, the device of the present invention can be adapted to be fastened to one of the animal's limbs, or to the animal's tail, as known in the art. The method is effective to protect an animal against arthropod pests such as fleas, ticks, flies, and mites, as well as lice and other ectoparasites. Animals that can benefit from the use of this method include domesticated animals such as dogs and cats, as well as farm animals, including cows, horses, goats and sheep, among others. The device of the present invention can also be used to control deer ticks to help reduce the incidence of Lyme Disease. For example, wild deer can be captured, the device fastened thereto, and the deer released.

The following example is illustrative only, and is not intended to limit the scope of the present invention.

6. EXAMPLE: TUBE COLLAR

The following study evaluated the efficacy of tube collars made according to the present invention with cypermethrin as the active ingredient, as compared to two commercially available collars and an untreated control group. The collars were evaluated for the control in dogs of either cat fleas or Brown Dog ticks.

Tube collars were prepared as follows. Tygon® R-3603 tubing (inner diameter ¼ inch; outer diameter 5/16 inch; wall thickness 1/32 inch) was cut into lengths of 17.5 inches. Near each end of the tubing, a mark was made on the outside of the tube with a Nalgene lab marker. Radio frequency sealing equipment (Fabricacione Electronicas, Buenos Aires, Argentina) was set up to an appropriate frequency, time and pressure to provide an acceptable seal of the tubing. One end of each tube was sealed at the first mark.

The following ingredients were mixed in the stated proportions: 51.4 wt % stearic acid; 10.1 wt % methyl palmitate; 10.2 wt % dimethicone; 22 wt % cypermethrin; 1.1 wt % BHT; and 5.2 wt % octyl methoxycinnamate. The ingredients were heated to 80° C. with stirring until a clear, brown, liquid homogenate was formed. A 10 ml syringe, without needle, was filled with the liquid homogenate which was then dispensed into each tube up to the second mark. The remaining open end of each tube was then sealed as above. Buckle fastening means were then attached to the ends of each tube to allow the tubes to be fastened as a collar around the neck of the dogs tested below. The tube collars were ready for use 3 days after manufacture.

Subject dogs were divided into two groups to be infested with either fleas or ticks. The dogs in each group were further divided into: (a) a control group of 6 dogs (no treatment); (b) a group of 6 dogs to wear a "Control Ultimate Flea Collar™" (Hartz Mountain®, Secaucus, N.J.; active ingredients: tetrachlorovinphos—14.55 wt %; methoprene—1.02 wt %); (c) a group of 6 dogs to wear a "Zodiac® 11-Month Flea Collar For Dogs" (Wellmark Int'l., Bensonville, Ill.; active ingredient: chlorpyrifos—8 wt %); and (d) a group of 6 dogs to wear a tube collar of the present invention (active ingredient: cypermethrin—10.2 wt % in relation to the total weight of the sealed tube without buckle). One hundred live fleas, or 50 live ticks, were applied to the dogs at weekly intervals throughout the study. Collar efficacy was measured initially by conducting live flea or live tick counts weekly for the first 44 days, and then biweekly thereafter up to 143 days. Percent reductions in fleas or ticks were calculated. The data collected are summarized in TABLES 1–4 below.

The tube collar of the present invention provided good protection against fleas throughout at least the entire test period. The performance of the tube collar was consistent over the entire test period and superior or equal to the two commercial collars tested. TABLES 1 and 2 demonstrate the superior performance against fleas of the tube collar of the present invention over the Hartz Mountain® Control Ultimate Flea Collar™. In fact, testing of the Hartz Mountain® Control Ultimate Flea Collar™ against fleas had to be discontinued on day 58 for lack of efficacy. TABLES 1 and 2 further demonstrate that the tube collar of the present invention was at least as effective against fleas as the Zodiac® 11-Month Flea Collar For Dogs.

The tube collar of the present invention also provided good protection against ticks throughout at least the entire test period. The performance of the tube collar was consistent over the entire test period and superior to both of the two commercial collars tested. TABLES 3 and 4 demonstrate the superior performance against ticks of the tube collar of the present invention over both the Hartz Mountain® Control Ultimate Flea Collar™ and the Zodiac® 11-Month Flea Collar For Dogs. In fact, testing of the Zodiac® 11-Month Flea Collar For Dogs against ticks had to be discontinued on day 59, and testing of the Hartz Mountain® Control Ultimate Flea Collar™ against ticks had to be discontinued on day 129, for lack of efficacy.

No adverse effects were observed during the above-described studies in dogs wearing the tube collar of the present invention. In addition, the animals' coats appeared noticeably fluffier than those of the dogs wearing either of the two commercial collars, or dogs in the untreated control group.

All patents, patent applications, and publications cited above are incorporated herein by reference in their entirety.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein, will become apparent to those skilled in the art from the foregoing description. Such modifications are intended to fall within the scope of the appended claims.

ture of (a) a gelling agent which consists of one or more saturated fatty acids or salts thereof, (b) an organic solvent which is a linear aliphatic ester, a silicone fluid, or a combination thereof, and (c) an active ingredient that can protect the animal against one or more arthropod pests, wherein the supporting membrane of the reservoir comprises a polymeric material that is permeable to the active ingredient;

TABLE 1

TOTAL NUMBER OF FLEAS*

| Collar | Day 9 | Day 16 | Day 23 | Day 30 | Day 37 | Day 44 | Day 58 | Day 72 | Day 86 | Day 100 | Day 114 | Day 128 | Day 142 |
|---|---|---|---|---|---|---|---|---|---|---|---|---|---|
| Control | 435 | 498 | 465 | 535 | 469 | 501 | 431 | 488 | 483 | 500 | 416 | 479 | 476 |
| Tube | 27 | 3 | 15 | 11 | 8 | 4 | 2 | 1 | 0 | 27 | 13 | 2 | 1 |
| Zodiac | 36 | 15 | 19 | 6 | 7 | 1 | 1 | 6 | 3 | 16 | 18 | 18 | 25 |
| Hartz | 66 | 28 | 106 | 115 | 126 | 82 | 127 | —[a] | — | — | — | — | — |

*Total fleas on 6 dogs per treatment.
[a]Treatment was discontinued.

TABLE 2

PERCENT REDUCTION OF FLEAS*

| Collar | Day 9 | Day 16 | Day 23 | Day 30 | Day 37 | Day 44 | Day 58 | Day 72 | Day 86 | Day 100 | Day 114 | Day 128 | Day 142 |
|---|---|---|---|---|---|---|---|---|---|---|---|---|---|
| Tube | 93.8 | 99.4 | 96.8 | 97.9 | 98.3 | 99.2 | 99.5 | 99.8 | 100.0 | 94.6 | 96.9 | 99.6 | 99.8 |
| Zodiac | 91.7 | 97.0 | 95.9 | 98.9 | 98.5 | 99.8 | 99.8 | 98.8 | 99.4 | 96.8 | 95.7 | 96.2 | 94.8 |
| Hartz | 84.8 | 94.4 | 77.2 | 78.5 | 73.1 | 83.6 | 70.5 | — | — | — | — | — | — |

*Average percent reduction of fleas per 6 dogs tested.

TABLE 3

TOTAL NUMBER OF TICKS*

| Collar | Day 9 | Day 16 | Day 24 | Day 30 | Day 38 | Day 45 | Day 59 | Day 73 | Day 87 | Day 101 | Day 115 | Day 129 | Day 143 |
|---|---|---|---|---|---|---|---|---|---|---|---|---|---|
| Control | 88 | 114 | 113 | 131 | 141 | 106 | 145 | 124 | 124 | 124 | 133 | 140 | 126 |
| Tube | 30 | 45 | 24 | 12 | 17 | 15 | 12 | 13 | 10 | 19 | 22 | 29 | 31 |
| Zodiac | 71 | 33 | 57 | 19 | 48 | 37 | 54 | —[a] | — | — | — | — | — |
| Hartz | 3 | 7 | 5 | 10 | 10 | 6 | 10 | 24 | 33 | 32 | 63 | 59 | —[a] |

*Total ticks on 6 dogs per treatment.
[a]Treatment was discontinued.

TABLE 4

PERCENT REDUCTION OF TICKS*

| Collar | Day 9 | Day 16 | Day 24 | Day 30 | Day 38 | Day 45 | Day 59 | Day 73 | Day 87 | Day 101 | Day 115 | Day 129 | Day 143 |
|---|---|---|---|---|---|---|---|---|---|---|---|---|---|
| Tube | 65.9 | 60.5 | 78.8 | 90.8 | 87.9 | 85.9 | 91.7 | 89.5 | 91.9 | 84.7 | 83.5 | 79.3 | 75.4 |
| Zodiac | 19.3 | 71.1 | 49.6 | 85.5 | 66.0 | 65.1 | 62.8 | — | — | — | — | — | — |
| Hartz | 96.6 | 93.9 | 95.6 | 92.4 | 92.9 | 94.3 | 93.1 | 80.7 | 73.4 | 74.2 | 52.6 | 57.9 | — |

*Average percent reduction of ticks per 6 dogs tested.

What is claimed is:

1. A device capable of the controlled, sustained release of an effective amount of an active ingredient that can protect an animal against arthropod pests, comprising:
   a reservoir having a supporting membrane comprising an outside surface, and an inside surface defining an enclosed cavity, and a gel contained within the enclosed cavity and in contact with the inside surface of the supporting membrane, said gel comprising the admixture of (a) a gelling agent which consists of one or more saturated fatty acids or salts thereof, (b) an organic solvent which is a linear aliphatic ester, a silicone fluid, or a combination thereof, and (c) an active ingredient that can protect the animal against one or more arthropod pests, wherein the supporting membrane of the reservoir comprises a polymeric material that is permeable to the active ingredient;
   and a fastening means for fastening the device to the animal.

2. The device of claim 1, wherein the polymeric material of the supporting membrane of the reservoir is selected from the group consisting of porous tetrafluoroethylene, polyethylene, polypropylene, polyamide, flexible polyacrylate, polyvinyl chloride, ethylenevinylacetate, polyolefin, polyurethane, silicone, and a combination thereof.

3. The device of claim 2, wherein the polymeric material of the supporting membrane of the reservoir is polyvinyl chloride.

4. The device of claim 1, wherein the fatty acid is selected from the group of fatty acids having an unbranched hydrocarbon chain from about $C_{15}$ to about $C_{17}$ in length.

5. The device of claim 4, wherein the fatty acid is a saturated fatty acid.

6. The device of claim 5, wherein the saturated fatty acid is selected from palmitic acid, stearic acid, and a combination thereof.

7. The device of claim 6, wherein the saturated fatty acid is stearic acid.

8. The device of claim 1, wherein the linear aliphatic ester is selected from the group consisting of linear aliphatic esters having from about 9 carbons to about 17 carbons in the chain.

9. The device of claim 8, wherein the linear aliphatic ester is selected from methyl caproate, methyl caprylate, methyl myristate, methyl palmitate, and a combination thereof.

10. The device of claim 9, wherein the linear aliphatic ester is methyl palmitate.

11. The device of claim 1, wherein the silicone fluid is selected from the group consisting of cyclomethicone, dimethicone, dimethicone copolyol, trimethylsilylamodimethicone, and a combination thereof.

12. The device of claim 11, wherein the silicone fluid is dimethicone.

13. The device of claim 1, wherein the organic solvent consists of a combination of methyl palmitate and dimethicone.

14. The device of claim 13, wherein the weight ratio of methyl palmitate and dimethicone ranges from about 90 wt % methyl palmitate:10 wt % dimethicone to about 10 wt % methyl palmitate:90 wt % dimethicone.

15. The device of claim 14, wherein the weight ratio of methyl palmitate and dimethicone ranges from about 60 wt % methyl palmitate:40 wt % dimethicone to about 40 wt % methyl palmitate:60 wt % dimethicone.

16. The device of claim 15, wherein the weight ratio of methyl palmitate and dimethicone is about 50 wt % methyl palmitate:50 wt % dimethicone.

17. The device of claim 1, wherein the active ingredient is an insecticide, an insect repellant, an insect growth regulator, or a combination thereof.

18. The device of claim 17, wherein the active ingredient is an insecticide selected from the group consisting of chlorinated hydrocarbons, organophosphates, pyrethrins, pyrethroids, carbamates, and a combination thereof.

19. The device of claim 18, wherein the active ingredient is selected from the group consisting of lindane, methoxychlor, permethrin, cypermethrin, dichlorvos, diazinon, chlorfenvinphos, bendiocarb, amitraz, chlorpyrifos, deltamethrin, sevin, and a combination thereof.

20. The device of claim 19, wherein the active ingredient is cypermethrin.

21. The device of claim 17, wherein the active ingredient is an insect repellant selected from the group consisting of DEET, citronella, permethrin, pyrethrin, and a combination thereof.

22. The device of claim 17, wherein the active ingredient is an insect growth regulator selected from the group consisting of methoprene, hydroprene, S-methoprene, S-hydroprene, dimilin, chromazine, and combinations thereof.

23. The device of claim 1, wherein the gel further comprises an anti-oxidant, an ultraviolet light blocker, or a combination thereof.

24. The device of claim 23, wherein the anti-oxidant is selected from the group consisting of butoxyhydroxytoluene, sodium sulfite, pyrazolone, thioglycolic acid, and a combination thereof.

25. The device of claim 23, wherein the ultraviolet light blocker is selected from the group consisting of octyl dimethyl para-amino benzoic acid (PABA), octyl methoxycinnamate, benzophenone 3, octyl salicylate, octocrylene, and a combination thereof.

26. The device of claim 1, wherein the gel comprises from about 45 wt % to about 55 wt % stearic acid, from about 15 wt % to about 25 wt % organic solvent, and from about 18 wt % to about 28 wt % active ingredient.

27. The device of claim 26, wherein the gel further comprises an anti-oxidant in a weight range of from about 1 wt % to about 7 wt % and an ultraviolet light blocker in a weight range of from about 1 wt % to about 7 wt %.

28. The device of claim 1, comprising a reservoir having a supporting membrane of polyvinyl chloride, said supporting membrane comprising an outside surface, and an inside surface defining an enclosed cavity, and a gel contained within the enclosed cavity and in contact with the inside surface of the supporting membrane, said gel comprising the admixture of stearic acid or a salt thereof, an organic solvent which is a combination of methyl palmitate and dimethicone, and an insecticide, insect repellant or insect growth regulator that can protect an animal against fleas and ticks, which active ingredient is capable of permeating through the supporting membrane; and a fastening means for fastening the device to the animal.

29. A method of protecting an animal against arthropod pests, comprising the step of fastening a device to the animal, said device comprising a reservoir having a supporting membrane comprising an outside surface, and an inside surface defining an enclosed cavity, and a gel contained within the enclosed cavity and in contact with the inside surface of the supporting membrane, said gel comprising the admixture of (a) a gelling agent which consists of one or more saturated fatty acids or salts thereof, (b) an organic solvent which is a linear aliphatic ester, a silicone fluid, or a combination thereof, and (c) an active ingredient that can protect the animal against one or more arthropod pests, wherein the supporting membrane of the reservoir comprises a polymeric material that is permeable to the active ingredient; and a fastening means for fastening the device to the animal.

\* \* \* \* \*